ň(12) United States Patent
Cao

(10) Patent No.: US 8,299,321 B2
(45) Date of Patent: Oct. 30, 2012

(54) NUCLEIC ACID MOLECULES AND OTHER MOLECULES ASSOCIATED WITH PLANTS AND USES THEREOF FOR PLANT IMPROVEMENT

(75) Inventor: Yongwei Cao, Chesterfield, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1135 days.

(21) Appl. No.: 11/980,366

(22) Filed: Oct. 31, 2007
(Under 37 CFR 1.47)

(65) Prior Publication Data
US 2009/0217414 A1      Aug. 27, 2009

Related U.S. Application Data

(63) Continuation-in-part of application No. 10/612,783, filed on Jul. 2, 2003, now abandoned, which is a continuation-in-part of application No. 09/371,146, filed on Aug. 9, 1999, now abandoned, which is a continuation-in-part of application No. 09/304,517, filed on May 6, 1999, now abandoned, said application No. 10/612,783 is a continuation-in-part of application No. 09/684,016, filed on Oct. 10, 2000, now abandoned, which is a continuation-in-part of application No. 09/654,617, filed on Sep. 5, 2000, now abandoned, said application No. 10/612,783 is a continuation-in-part of application No. 09/985,678, filed on Nov. 5, 2001, now abandoned, which is a continuation of application No. 09/304,517, filed on May 6, 1999, now abandoned, said application No. 10/612,783 is a continuation-in-part of application No. 09/816,660, filed on Mar. 26, 2001, now abandoned, which is a continuation of application No. 09/733,089, filed on Dec. 11, 2000, now abandoned, said application No. 10/612,783 is a continuation-in-part of application No. 10/155,881, filed on May 22, 2002, now abandoned, and a continuation-in-part of application No. 09/333,535, filed on Jun. 14, 1999, now abandoned, said application No. 10/612,783 is a continuation-in-part of application No. 09/615,606, filed on Jul. 13, 2000, now abandoned, said application No. 10/612,783 is a continuation-in-part of application No. 09/394,745, filed on Sep. 15, 1999, now abandoned, and a continuation-in-part of application No. 09/565,306, filed on May 4, 2000, now abandoned, said application No. 10/612,783 is a continuation-in-part of application No. 09/553,094, filed on Apr. 18, 2000, now abandoned, and a continuation-in-part of application No. 09/440,687, filed on Nov. 16, 1999, now abandoned, and a continuation-in-part of application No. 09/552,086, filed on Apr. 19, 2000, now abandoned, said application No. 10/612,783 is a continuation-in-part of application No. 09/531,113, filed on Mar. 22, 2000, now abandoned, said application No. 10/612,783 is a continuation-in-part of application No. 09/692,257, filed on Oct. 19, 2000, now abandoned, and a continuation-in-part of application No. 09/565,240, filed on May 8, 2000, now abandoned, and a continuation-in-part of application No. 09/619,643, filed on Jul. 19, 2000, now abandoned, and a continuation-in-part of application No. 09/663,423, filed on Sep. 15, 2000, now abandoned, said application No. 10/612,783 is a continuation-in-part of application No. 09/669,817, filed on Sep. 26, 2000, now abandoned, and a continuation-in-part of application No. 09/696,664, filed on Oct. 25, 2000, now abandoned, and a continuation-in-part of application No. 09/837,604, filed on Apr. 18, 2001, now abandoned, said application No. 10/612,783 is a continuation-in-part of application No. 09/849,526, filed on May 7, 2001, now abandoned, said application No. 10/612,783 is a continuation-in-part of application No. 09/874,708, filed on Jun. 5, 2001, now abandoned, said application No. 10/612,783 is a continuation-in-part of application No. 09/873,402, filed on Jun. 5, 2001, now abandoned, said application No. 10/612,783 is a continuation-in-part of application (Continued)

(51) Int. Cl.
| | |
|---|---|
| *C12N 15/00* | (2006.01) |
| *A01H 5/00* | (2006.01) |
| *A01H 1/00* | (2006.01) |
| *C07H 21/04* | (2006.01) |
| *C07K 14/415* | (2006.01) |

(52) U.S. Cl. ......... 800/295; 435/6.1; 435/468; 435/419; 435/320.1; 435/183; 530/370; 536/23.6; 800/278

(58) Field of Classification Search .............. 435/6, 468, 435/419, 320.1, 183, 6.1; 530/370; 536/23.6; 800/278, 295
See application file for complete search history.

(56) References Cited

U.S. PATENT DOCUMENTS

2003/0233670 A1* 12/2003 Edgerton et al. .............. 800/278

OTHER PUBLICATIONS

Degtyarenko et al., "Molecular evolution of P450 superfamily and P450-containing monooxygenase systems," *FEBS*, 332(1,2):1-8 (1993).

(Continued)

*Primary Examiner* — Phuong Bui
(74) *Attorney, Agent, or Firm* — Lawrence M. Lavin, Jr.; Ying-Hong Liu; Arnold & Porter LLP

(57) ABSTRACT

Polynucleotides useful for improvement of plants are provided. In particular, polynucleotide sequences are provided from plant sources. Polypeptides encoded by the polynucleotide sequences are also provided. The disclosed polynucleotides and polypeptides find use in production of transgenic plants to produce plants having improved properties.

8 Claims, No Drawings

Related U.S. Application Data

No. 09/865,419, filed on May 29, 2001, now abandoned, said application No. 10/612,783 is a continuation-in-part of application No. 09/865,439, filed on May 29, 2001, now abandoned, said application No. 10/612,783 is a continuation-in-part of application No. 09/938,294, filed on Aug. 24, 2001, now abandoned, said application No. 10/612,783 is a continuation-in-part of application No. 10/219,999, filed on Aug. 15, 2002, now abandoned.

(60) Provisional application No. 60/089,524, filed on Jun. 16, 1998, provisional application No. 60/144,084, filed on Jul. 16, 1999, provisional application No. 60/132,860, filed on May 7, 1999, provisional application No. 60/130,464, filed on Apr. 22, 1999, provisional application No. 60/141,132, filed on Jun. 28, 1999, provisional application No. 60/141,139, filed on Jun. 28, 1999, provisional application No. 60/141,135, filed on Jun. 28, 1999, provisional application No. 60/130,174, filed on Apr. 20, 1999, provisional application No. 60/125,818, filed on Mar. 23, 1999, provisional application No. 60/141,132, filed on Jun. 28, 1999, provisional application No. 60/141,139, filed on Jun. 28, 1999, provisional application No. 60/141,135, filed on Jun. 28, 1999, provisional application No. 60/125,817, filed on Mar. 23, 1999, provisional application No. 60/130,174, filed on Apr. 20, 1999, provisional application No. 60/154,375, filed on Sep. 17, 1999, provisional application No. 60/197,872, filed on Apr. 19, 2000, provisional application No. 60/202,214, filed on May 8, 2000, provisional application No. 60/211,750, filed on Jun. 15, 2000, provisional application No. 60/209,830, filed on Jun. 6, 2000, provisional application No. 60/208,063, filed on May 31, 2000, provisional application No. 60/207,458, filed on May 30, 2000, provisional application No. 60/228,466, filed on Aug. 29, 2000, provisional application No. 60/312,544, filed on Aug. 15, 2001, provisional application No. 60/324,109, filed on Sep. 21, 2001.

(56) References Cited

OTHER PUBLICATIONS

Werck-Reichhart et al., "Cytochromes P450: a success story," *Genome Biology*, 1(6) (2000).
NCBI Website, BLASTN Accession No. Q05JG2 dated Jul. 1, 2008.
NCBI Website, BLASTN Accession No. NP_001047855 dated Feb. 14, 2008.
NCBI Website, BLASTN Accession No. ABB71585 dated Mar. 5, 2006.
NCBI Website, BLASTN Accession No. NP_567581 dated May 22, 2008.
NCBI Website, BLASTN Accession No. NP_851136 dated May 22, 2008.
NCBI Website, BLASTN Accession No. ABA55732 dated Aug. 4, 2006.
NCBI Website, BLASTN Accession No. CAO63746 dated Oct. 8, 2007.
NCBI Website, BLASTN Accession No. ABC86558 dated Sep. 1, 2006.
NCBI Website, BLASTN Accession No. ABQ65856 dated Jan. 31, 2008.
NCBI Website, BLASTN Accession No. BAG12741 dated Mar. 8, 2008.
NCBI Website, BLASTN Accession No. BAG12743 dated Mar. 8, 2008.
NCBI Website, BLASTN Accession No. CAA16713 dated Nov. 14, 2006.
NCBI Website, BLASTN Accession No. NP_974574 dated May 22, 2008.
NCBI Website, BLASTN Accession No. NP_199347 dated May 22, 2008.
NCBI Website, BLASTN Accession No. CAO61343 dated Oct. 8, 2007.
NCBI Website, BLASTN Accession No. A2Z212 dated Jul. 1, 2008.
NCBI Website, BLASTN Accession No. NP_001063366 dated Feb. 14, 2008.
NCBI Website, BLASTN Accession No. BAG12742 dated Mar. 8, 2008.
NCBI Website, BLASTN Accession No. CAO47816 dated Oct. 8, 2007.
NCBI Website, BLASTN Accession No. CAN79871 dated Feb. 5, 2008.
NCBI Website, BLASTN Accession No. NP_566628 dated May 22, 2008.
NCBI Website, BLASTN Accession No. NP_180473 dated May 22, 2008.
NCBI Website, BLASTN Accession No. ABA55733 dated Aug. 4, 2006.
NCBI Website, BLASTN Accession No. ABX38720 dated Dec. 1, 2007.
NCBI Website, BLASTN Accession No. ABB71586 dated Mar. 5, 2006.
NCBI Website, BLASTN Accession No. AAZ23260 dated Feb. 16, 2006.
NCBI Website, BLASTN Accession No. BAD38475 dated Feb. 16, 2008.
NCBI Website, BLASTN Accession No. ABC86559 dated Sep. 1, 2006.
NCBI Website, BLASTN Accession No. EAZ07320 dated Feb. 9, 2007.
NCBI Website, BLASTN Accession No. Q09J78 dated Jul. 1, 2008.
NCBI Website, BLASTIN Accession No. BAG12744 dated Mar. 8, 2008.
NCBI Website, BLASTN Accession No. NP_001062021 dated Feb. 14, 2008.
NCBI Website, BLASTN Accession No. CAO21623 dated Oct. 8, 2007.
NCBI Website, BLASTN Accession No. ABC59109 dated Jun. 6, 2007.
NCBI Website, BLASTN Accession No. BAB02968 dated Feb. 14, 2004.
NCBI Website, BLASTN Accession No. CAO71844 dated Oct. 8, 2007.
NCBI Website, BLASTN Accession No. ABC86560 dated Sep. 1, 2006.
NCBI Website, BLASTN Accession No. ABW81069 dated Mar. 30, 2008.
NCBI Website, BLASTN Accession No. CAN82146 dated Feb. 5, 2008.
NCBI Website, BLASTN Accession No. CAN71726 dated Feb. 5, 2008.
NCBI Website, BLASTN Accession No. EAZ43058 dated Feb. 12, 2007.
NCBI Website, BLASTN Accession No. ABC68415 dated Aug. 8, 2006.
NCBI Website, BLASTN Accession No. AB277270 dated Feb. 15, 2008.
NCBI Website, BLASTN Accession No. DQ887714 dated Oct. 16, 2006.
NCBI Website, BLASTN Accession No. NM_001054390 dated Feb. 14, 2008.
NCBI Website, BLASTN Accession No. AK067007 dated Feb. 16, 2008.
NCBI Website, BLASTN Accession No. AB239299 dated Aug. 12, 2006.

NCBI Website, BLASTN Accession No. DQ145932 dated Mar. 5, 2006.
NCBI Website, BLASTN Accession No. AP005825 dated Feb. 16, 2008.
NCBI Website, BLASTN Accession No. AP004052 dated Feb. 16, 2008.
NCBI Website, BLASTN Accession No. AK288402 dated Feb. 16, 2008.
NCBI Website, BLASTN Accession No. NM_001069901 dated Feb. 14, 2008.
NCBI Website, BLASTN Accession No. DQ887715 dated Oct. 16, 2006.
NCBI Website, BLASTN Accession No. AP008208 dated May 19, 2007.
NCBI Website, BLASTN Accession No. NM_001068556 dated Feb. 14, 2008.
NCBI Website, BLASTN Accession No. AK120757 dated Feb. 16, 2008.
NCBI Website, BLASTN Accession No. DQ145933 dated Mar. 5, 2006.
NCBI Website, BLASTN Accession No. AB235919 dated Mar. 8, 2008.
NCBI Website, BLASTN Accession No. EF377341 dated Jan. 31, 2008.
NCBI Website, BLASTN Accession No. DQ352541 dated Sep. 1, 2006.
NCBI Website, BLASTN Accession No. NM_118043 dated May 22, 2008.
NCBI Website, BLASTN Accession No. AY091446 dated Sep. 18, 2002.
NCBI Website, BLASTN Accession No. AY050980 dated Sep. 18, 2002.
NCBI Website, BLASTN Accession No. AB122149 dated Apr. 17, 2004.
NCBI Website, BLASTN Accession No. NM_202845 dated May 22, 2008.
NCBI Website, BLASTN Accession No. AY107506 dated Jun. 6, 2008.
NCBI Website, BLASTN Accession No. BX828383 dated Feb. 6, 2004.
NCBI Website, BLASTN Accession No. AP008215 dated May 19, 2007.
NCBI Website, BLASTN Accession No. AP006057 dated Feb. 16, 2008.
NCBI Website, BLASTN Accession No. DQ340252 dated Aug. 8, 2006.
NCBI Website, BLASTN Accession No. AB235917 dated Mar. 8, 2008.
NCBI Website, BLASTN Accession No. AP008214 dated May 19, 2007.
NCBI Website, BLASTN Accession No. AP004457 dated Feb. 16, 2008.
NCBI Website, BLASTN Accession No. NM_123902 dated May 22, 2008.
NCBI Website, BLASTN Accession No. NM_180805 dated May 22, 2008.
NCBI Website, BLASTN Accession No. AY102136 dated May 16, 2002.
NCBI Website, BLASTN Accession No. AY065065 dated Jan. 7, 2002.
NCBI Website, BLASTN Accession No. AB122150 dated Apr. 17, 2004.
NCBI Website, BLASTN Accession No. BX831670 dated Feb. 6, 2004.
Sasaki et al., Accession No. AP004129, GenEmbl Database, 2001, Result 5.
GenBank Accession No. AF296079 (Jan. 24, 2001) (1 page).
Ober et al., Deoxyhypusine Synthase from Tobacco cDNA Isolation, Characterization, and Bacterial Expression of an Enzyme with Extended Substrate Specificity, *The Journal of Biological Chemistry*, 274(45):32040-32047 (1999).

* cited by examiner

NUCLEIC ACID MOLECULES AND OTHER MOLECULES ASSOCIATED WITH PLANTS AND USES THEREOF FOR PLANT IMPROVEMENT

CROSS-REFERENCE TO RELATED APPLICATIONS

This application is a continuation-in-part under 35 U.S.C. §120 of U.S. application Ser. No. 10/612,783, filed on Jul. 2, 2003 (abandoned), which is hereby incorporated by reference in its entirety, including its Sequence Listing and Table 1. U.S. application Ser. No. 10/612,783 claims priority under 35 U.S.C. §120 as a continuation-in-part of U.S. application Ser. No. 09/371,146, filed Aug. 9, 1999 (abandoned), which is a continuation-in-part of U.S. application Ser. No. 09/304,517, filed May 6, 1999, (abandoned). U.S. application Ser. No. 10/612,783 also claims priority under 35 U.S.C. §120 as a continuation-in-part of U.S. application Ser. No. 09/684,016, filed Oct. 10, 2000 (abandoned), which is a continuation-in-part of U.S. application Ser. No. 09/654,617, filed Sep. 5, 2000 (abandoned). U.S. application Ser. No. 10/612,783 also claims priority under 35 U.S.C. §120 as a continuation-in-part of U.S. application Ser. No. 09/985,678, filed Nov. 5, 2001 (abandoned), which is a continuation of U.S. application Ser. No. 09/304,517, filed May 6, 1999, (abandoned). U.S. application Ser. No. 10/612,783 also claims priority under 35 U.S.C. §120 as a continuation-in-part of U.S. application Ser. No. 09/816,660, filed Mar. 26, 2001 (abandoned), which is a continuation of U.S. application Ser. No. 09/733,089, filed Dec. 11, 2000, (abandoned). U.S. application Ser. No. 10/612,783 also claims priority under 35 U.S.C. §120 as a continuation-in-part of U.S. application Ser. No. 10/155,881, filed May 22, 2002 (abandoned). U.S. application Ser. No. 10/612,783 also claims priority under 35 U.S.C. §120 as a continuation-in-part of U.S. application Ser. No. 09/333,535, filed Jun. 14, 1999 (abandoned), which claims the benefit of U.S. Application Ser. No. 60/089,524, filed Jun. 16, 1998. U.S. application Ser. No. 10/612,783 also claims priority under 35 U.S.C. §120 as a continuation-in-part of U.S. application Ser. No. 09/615,606, filed Jul. 13, 2000 (abandoned), which claims the benefit of U.S. Application Ser. No. 60/144,084, filed Jul. 16, 1999. U.S. application Ser. No. 10/612,783 also claims priority under 35 U.S.C. §120 as a continuation-in-part of U.S. application Ser. No. 09/394,745, filed Sep. 15, 1999 (abandoned). U.S. application Ser. No. 10/612,783 also claims priority under 35 U.S.C. §120 as a continuation-in-part of U.S. application Ser. No. 09/565,306, filed May 4, 2000 (abandoned), which claims the benefit of U.S. Application Ser. No. 60/132,860, filed May 7, 1999. U.S. application Ser. No. 10/612,783 also claims priority under 35 U.S.C. §120 as a continuation-in-part of U.S. application Ser. No. 09/553,094, filed Apr. 18, 2000 (abandoned). U.S. application Ser. No. 10/612,783 also claims priority under 35 U.S.C. §120 as a continuation-in-part of U.S. application Ser. No. 09/440,687, filed Nov. 16, 1999 (abandoned). U.S. application Ser. No. 10/612,783 also claims priority under 35 U.S.C. §120 as a continuation-in-part of U.S. application Ser. No. 09/552,086, filed Apr. 19, 2000 (abandoned), which claims the benefit of U.S. Application Ser. No. 60/130,464, filed Apr. 22, 1999, and also the benefit of U.S. Application Ser. No. 60/141,132, filed Jun. 28, 1999, and also the benefit of U.S. Application Ser. No. 60/141,139, filed Jun. 28, 1999, and also the benefit of U.S. Application Ser. No. 60/141,135, filed Jun. 28, 1999, and also the benefit of U.S. Application Ser. No. 60/130,174, filed Apr. 20, 1999. U.S. application Ser. No. 10/612,783 also claims priority under 35 U.S.C. §120 as a continuation-in-part of U.S. application Ser. No. 09/531,113, filed Mar. 22, 2000 (abandoned), which claims the benefit of U.S. Application Ser. No. 60/125,818, filed Mar. 23, 1999, and also the benefit of U.S. Application Ser. No. 60/141,132, filed Jun. 28, 1999, and also the benefit of U.S. Application Ser. No. 60/141,139, filed Jun. 28, 1999, and also the benefit of U.S. Application Ser. No. 60/141,135, filed Jun. 28, 1999, and also the benefit of U.S. Application Ser. No. 60/125,817, filed Mar. 23, 1999, and also the benefit of U.S. Application Ser. No. 60/130,174, filed Apr. 20, 1999. U.S. application Ser. No. 10/612,783 also claims priority under 35 U.S.C. §120 as a continuation-in-part of U.S. application Ser. No. 09/692,257, filed Oct. 19, 2000 (abandoned). U.S. application Ser. No. 10/612,783 also claims priority under 35 U.S.C. §120 as a continuation-in-part of U.S. application Ser. No. 09/565,240, filed May 8, 2000 (abandoned). U.S. application Ser. No. 10/612,783 also claims priority under 35 U.S.C. §120 as a continuation-in-part of U.S. application Ser. No. 09/619,643, filed Jul. 19, 2000 (abandoned). U.S. application Ser. No. 10/612,783 also claims priority under 35 U.S.C. §120 as a continuation-in-part of U.S. application Ser. No. 09/663,423, filed Sep. 15, 2000 (abandoned), which claims the benefit of U.S. Application Ser. No. 60/154,375, filed Sep. 17, 1999. U.S. application Ser. No. 10/612,783 also claims priority under 35 U.S.C. §120 as a continuation-in-part of U.S. application Ser. No. 09/669,817, filed Sep. 26, 2000 (abandoned). U.S. application Ser. No. 10/612,783 also claims priority under 35 U.S.C. §120 as a continuation-in-part of U.S. application Ser. No. 09/696,664, filed Oct. 25, 2000 (abandoned). U.S. application Ser. No. 10/612,783 also claims priority under 35 U.S.C. §120 as a continuation-in-part of U.S. application Ser. No. 09/837,604, filed Apr. 18, 2001 (abandoned), which claims the benefit of U.S. Application Ser. No. 60/197,872, filed Apr. 19, 2000. U.S. application Ser. No. 10/612,783 also claims priority under 35 U.S.C. §120 as a continuation-in-part of U.S. application Ser. No. 09/849,526, filed May 7, 2001 (abandoned), which claims the benefit of U.S. Application Ser. No. 60/202,214, filed May 8, 2000. U.S. application Ser. No. 10/612,783 also claims priority under 35 U.S.C. §120 as a continuation-in-part of U.S. application Ser. No. 09/874,708, filed Jun. 5, 2001 (abandoned), which claims the benefit of U.S. Application Ser. No. 60/211,750, filed Jun. 15, 2000. U.S. application Ser. No. 10/612,783 also claims priority under 35 U.S.C. §120 as a continuation-in-part of U.S. application Ser. No. 09/873,402, filed Jun. 5, 2001 (abandoned), which claims the benefit of U.S. Application Ser. No. 60/209,830, filed Jun. 6, 2000. U.S. application Ser. No. 10/612,783 also claims priority under 35 U.S.C. §120 as a continuation-in-part of U.S. application Ser. No. 09/865,419, filed May 29, 2001 (abandoned), which claims the benefit of U.S. Application Ser. No. 60/208,063, filed May 31, 2000. U.S. application Ser. No. 10/612,783 also claims priority under 35 U.S.C. §120 as a continuation-in-part of U.S. application Ser. No. 09/865,439, filed May 29, 2001 (abandoned), which claims the benefit of U.S. Application Ser. No. 60/207,458, filed May 30, 2000. U.S. application Ser. No. 10/612,783 also claims priority under 35 U.S.C. §120 as a continuation-in-part of U.S. application Ser. No. 09/938,294, filed Aug. 24, 2001 (abandoned), which claims the benefit of U.S. Application Ser. No. 60/228,466, filed Aug. 29, 2000. U.S. application Ser. No. 10/612,783 also claims priority under 35 U.S.C. §120 as a continuation-in-part of U.S. application Ser. No. 10/219,999, filed Aug. 15, 2002 (abandoned), which claims the benefit of U.S. Application Ser. No. 60/312,544, filed Aug. 15, 2001, and also claims the benefit of U.S. Application Ser. No. 60/324,109, filed Sep. 21, 2001. All of the above-referenced applications are hereby incorporated by reference in their entireties, including their respective sequence listings and tables.

INCORPORATION OF SEQUENCE LISTING

Two copies of the sequence listing (Seq. Listing Copy 1 and Seq. Listing Copy 2) and a computer-readable form of the sequence listing, all on CD-Rs, each containing the file named pa_01260.rpt, which is 25,669,717 bytes (measured in MS-DOS) and was created on Oct. 29, 2007, are herein incorporated by reference.

INCORPORATION OF SEQUENCE LISTING

An electronic equivalent of a paper copy of the Sequence Listing containing the file named "53373.CorrSeqlist.pdf", which is 23,229,074 bytes in size (measured in MS-DOS) and which was created on Feb. 26, 2009, and a computer-readable form of the Sequence Listing containing the file named "53373.CorrSeqlist.txt", which is 26,419,279 bytes in size (measured in MS-DOS) and which was created on Feb. 25, 2009, are submitted herewith electronically via EFS web and are herein incorporated by reference.

polynucleotides and polypeptides of this invention are useful for improvement of one or more important properties in plants.

The present invention also provides fragments of the polynucleotides of the present invention for use, for example as probes or molecular markers. Such fragments comprise at least 15 consecutive nucleotides in a sequence selected from the group consisting of SEQ ID NOs: 1-9677 and complements thereof. Polynucleotide fragments of the present invention are useful as primers for PCR amplification and in hybridization assays such as transcription profiling assays or marker assays, e.g. high throughput assays where the oligonucleotides are provided in high-density arrays on a substrate. The present invention also provides homologs of the polynucleotide and polypeptides of the present invention.

This invention also provides DNA constructs comprising polynucleotides provided herein. Of particular interest are recombinant DNA constructs, wherein said constructs comprise a polynucleotide selected from the group consisting of:
(a) a polynucleotide comprising a nucleic acid sequence selected from the group consisting of SEQ ID NOs: 1-9677;

LENGTHY TABLES

The patent contains a lengthy table section. A copy of the table is available in electronic form from the USPTO web site (http://seqdata.uspto.gov/?pageRequest=docDetail&DocID=US08299321B2). An electronic copy of the table will also be available from the USPTO upon request and payment of the fee set forth in 37 CFR 1.19(b)(3).

FIELD OF THE INVENTION

Disclosed herein are inventions in the field of plant biochemistry and genetics. More specifically polynucleotides for use in plant improvement are provided, in particular, sequences from *Zea mays*, *Oryza sativa*, and *Glycine max* and the polypeptides encoded by such cDNAs are disclosed. Methods of using the polynucleotides for production of transgenic plants with improved biological characteristics are disclosed.

BACKGROUND OF THE INVENTION

The ability to develop transgenic plants with improved traits depends in part on the identification of genes that are useful for production of transformed plants for expression of novel polypeptides. In this regard, the discovery of the polynucleotide sequences of such genes, and the polypeptide encoding regions of genes, is needed. Molecules comprising such polynucleotides may be used, for example, in DNA constructs useful for imparting unique genetic properties into transgenic plants.

SUMMARY OF THE INVENTION

This invention provides isolated and purified polynucleotides comprising DNA sequences and the polypeptides encoded by such molecules from *Zea mays*, *Oryza sativa*, and *Glycine max*. Polynucleotide sequences of the present invention are provided in the attached Sequence Listing as SEQ ID NOs: 1-9677. Polypeptides of the present invention are provided as SEQ ID NOs: 9678-12046. Preferred subsets of the (b) a polynucleotide encoding a polypeptide having an amino acid sequence selected from the group consisting of SEQ ID NOs: 9678-12046;
(c) a polynucleotide comprising a nucleic acid sequence complementary to a nucleic acid sequence selected from the group consisting of SEQ ID NOs: 1-9677;
(d) a polynucleotide having at least 70% sequence identity to a polynucleotide of (a), (b) or (c);
(e) a polynucleotide encoding a polypeptide having at least 80% sequence identity to a polypeptide having an amino acid sequence selected from the group consisting of SEQ ID NOs: 9678-12046;
(f) a polynucleotide comprising a promoter functional in a plant cell, operably joined to a coding sequence for a polypeptide having at least 80% sequence identity to a polypeptide having an amino acid sequence selected from the group consisting of SEQ ID NOs: 9678-12046, wherein said encoded polypeptide is a functional homolog of said polypeptide having an amino acid sequence selected from the group consisting of SEQ ID NOs: 9678-12046; and
(g) a polynucleotide comprising a promoter functional in a plant cell, operably joined to a coding sequence for a polypeptide having an amino acid sequence selected from the group consisting of SEQ ID NOs: 9678-12046, wherein transcription of said coding sequence produces an RNA molecule having sufficient complementarity to a polynucleotide encoding said polypeptide to result in decreased expression of said polypeptide when said construct is expressed in a plant cell.

Such constructs are useful for production of transgenic plants having at least one improved property as the result of expression of a polypeptide of this invention. Improved properties of interest include yield, disease resistance, growth rate, stress tolerance and others as set forth in more detail herein.

The present invention also provides a method of modifying plant protein activity by inserting into cells of said plant an antisense construct comprising a promoter which functions in plant cells, a polynucleotide comprising a polypeptide coding sequence operably linked to said promoter, wherein said protein coding sequence is oriented such that transcription from said promoter produces an RNA molecule having sufficient complementarity to a polynucleotide encoding said polypeptide to result in decreased expression of said polypeptide when said construct is expressed in a plant cell.

This invention also provides a transformed organism, particularly a transformed plant, preferably a transformed crop plant, comprising a recombinant DNA construct of the present invention.

DETAILED DESCRIPTION OF THE INVENTION

The present invention provides polynucleotides, or nucleic acid molecules, representing DNA sequences and the polypeptides encoded by such polynucleotides from *Zea mays, Oryza sativa*, and *Glycine max*. The polynucleotides and polypeptides of the present invention find a number of uses, for example in recombinant DNA constructs, in physical arrays of molecules, and for use as plant breeding markers. In addition, the nucleotide and amino acid sequences of the polynucleotides and polypeptides find use in computer based storage and analysis systems.

Depending on the intended use, the polynucleotides of the present invention may be present in the form of DNA, such as cDNA or genomic DNA, or as RNA, for example mRNA. The polynucleotides of the present invention may be single or double stranded and may represent the coding, or sense strand of a gene, or the non-coding, antisense, strand.

The polynucleotides of the present invention find particular use in generation of transgenic plants to provide for increased or decreased expression of the polypeptides encoded by the cDNA polynucleotides provided herein. As a result of such biotechnological applications, plants, particularly crop plants, having improved properties are obtained. Crop plants of interest in the present invention include, but are not limited to soy, cotton, canola, maize, wheat, sunflower, sorghum, alfalfa, barley, millet, rice, tobacco, fruit and vegetable crops, and turf grass. Of particular interest are uses of the disclosed polynucleotides to provide plants having improved yield resulting from improved utilization of key biochemical compounds, such as nitrogen, phosphorous and carbohydrate, or resulting from improved responses to environmental stresses, such as cold, heat, drought, salt, and attack by pests or pathogens. Polynucleotides of the present invention may also be used to provide plants having improved growth and development, and ultimately increased yield, as the result of modified expression of plant growth regulators or modification of cell cycle or photosynthesis pathways. Other traits of interest that may be modified in plants using polynucleotides of the present invention include flavonoid content, seed oil and protein quantity and quality, herbicide tolerance, and rate of homologous recombination.

The term "isolated" is used herein in reference to purified polynucleotide or polypeptide molecules. As used herein, "purified" refers to a polynucleotide or polypeptide molecule separated from substantially all other molecules normally associated with it in its native state. More preferably, a substantially purified molecule is the predominant species present in a preparation. A substantially purified molecule may be greater than 60% free, preferably 75% free, more preferably 90% free, and most preferably 95% free from the other molecules (exclusive of solvent) present in the natural mixture. The term "isolated" is also used herein in reference to polynucleotide molecules that are separated from nucleic acids which normally flank the polynucleotide in nature. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The terms "isolated" and "purified" as used herein are not intended to encompass molecules present in their native state.

As used herein a "transgenic" organism is one whose genome has been altered by the incorporation of foreign genetic material or additional copies of native genetic material, e.g. by transformation or recombination.

It is understood that the molecules of the invention may be labeled with reagents that facilitate detection of the molecule. As used herein, a label can be any reagent that facilitates detection, including fluorescent labels, chemical labels, or modified bases, including nucleotides with radioactive elements, e.g. $^{32}P$, $^{33}P$, $^{35}S$ or $^{125}I$ such as $^{32}P$ deoxycytidine-5'-triphosphate ($^{32}PdCTP$).

Polynucleotides of the present invention are capable of specifically hybridizing to other polynucleotides under certain circumstances. As used herein, two polynucleotides are said to be capable of specifically hybridizing to one another if the two molecules are capable of forming an anti-parallel, double-stranded nucleic acid structure. A nucleic acid molecule is said to be the "complement" of another nucleic acid molecule if the molecules exhibit complete complementarity. As used herein, molecules are said to exhibit "complete complementarity" when every nucleotide in each of the molecules is complementary to the corresponding nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are known to those skilled in the art and can be found, for example in *Molecular Cloning: A Laboratory Manual*, 3rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology*, John Wiley & Sons, N.Y. (1989). Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

As used herein "sequence identity" refers to the extent to which two optimally aligned polynucleotide or peptide sequences are invariant throughout a window of alignment of components, e.g. nucleotides or amino acids. An "identity fraction" for aligned segments of a test sequence and a reference sequence is the number of identical components which are shared by the two aligned sequences divided by the total number of components in the reference sequence segment, i.e. the entire reference sequence or a smaller defined part of the reference sequence. "Percent identity" is the identity fraction times 100. Comparison of sequences to determine percent identity can be accomplished by a number of well-known methods, including for example by using mathematical algorithms, such as those in the BLAST suite of sequence analysis programs.

Polynucleotides—This invention provides polynucleotides comprising regions that encode polypeptides. The encoded polypeptides may be the complete protein encoded by the gene represented by the polynucleotide, or may be fragments of the encoded protein. Preferably, polynucleotides provided herein encode polypeptides constituting a substantial portion of the complete protein, and more preferentially, constituting a sufficient portion of the complete protein to provide the relevant biological activity.

Of particular interest are polynucleotides of the present invention that encode polypeptides involved in one or more important biological functions in plants. Such polynucleotides may be expressed in transgenic plants to produce plants having improved phenotypic properties and/or improved response to stressful environmental conditions. See, for example, Table 1 of U.S. application Ser. No. 10/612,783 and Table 2 and Table 3 of the present application for a list of improved plant properties and responses, and the SEQ ID NOs: 1-9677 representing the polynucleotides that may be expressed in transgenic plants to impart such improvements.

Polynucleotides of the present invention are generally used to impart such biological properties by providing for enhanced protein activity in a transgenic organism, preferably a transgenic plant, although in some cases, improved properties are obtained by providing for reduced protein activity in a transgenic plant. Reduced protein activity and enhanced protein activity are measured by reference to a wild type cell or organism and can be determined by direct or indirect measurement. Direct measurement of protein activity might include an analytical assay for the protein, per se, or enzymatic product of protein activity. Indirect assay might include measurement of a property affected by the protein. Enhanced protein activity can be achieved in a number of ways, for example by overproduction of mRNA encoding the protein or by gene shuffling. One skilled in the are will know methods to achieve overproduction of mRNA, for example by providing increased copies of the native gene or by introducing a construct having a heterologous promoter linked to the gene into a target cell or organism. Reduced protein activity can be achieved by a variety of mechanisms including antisense, mutation or knockout. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

The polynucleotides of this invention represent cDNA sequences from species such as Zea mays, Oryza sativa, and Glycine max. Nucleic acid sequences of the polynucleotides of the present invention are provided as SEQ ID NOs: 1-9677 in the sequence listing of the present application and additionally in U.S. application Ser. No. 10/612,783 as SEQ ID NOs: 1-3549, wherein SEQ ID NOs: 1-491 represent sequences derived from Glycine max, SEQ ID NOs: 492-3025 represent sequences derived from Zea mays, and SEQ ID NOs: 3026-3549 represent sequences derived from Oryza sativa.

A subset of the nucleic molecules of this invention includes fragments of the disclosed polynucleotides consisting of oligonucleotides of at least 15, preferably at least 16 or 17, more preferably at least 18 or 19, and even more preferably at least 20 or more, consecutive nucleotides. Such oligonucleotides are fragments of the larger molecules having a sequence selected from the group of polynucleotide sequences consisting of SEQ ID NOs: 1-9677, and find use, for example as probes and primers for detection of the polynucleotides of the present invention.

Also of interest in the present invention are variants of the polynucleotides provided herein. Such variants may be naturally occurring, including homologous polynucleotides from the same or a different species, or may be non-natural variants, for example polynucleotides synthesized using chemical synthesis methods, or generated using recombinant DNA techniques. With respect to nucleotide sequences, degeneracy of the genetic code provides the possibility to substitute at least one base of the protein encoding sequence of a gene with a different base without causing the amino acid sequence of the polypeptide produced from the gene to be changed. Hence, the DNA of the present invention may also have any base sequence that has been changed from SEQ ID NOs: 1-9677 by substitution in accordance with degeneracy of the genetic code. References describing codon usage include: Carels et al., J. Mol. Evol. 46: 45 (1998) and Fennoy et al., Nucl. Acids Res. 21(23): 5294 (1993).

Polynucleotides of the present invention that are variants of the polynucleotides provided herein will generally demonstrate significant identity with the polynucleotides provided herein. Of particular interest are polynucleotide homologs having at least about 60% sequence identity, at least about 70% sequence identity, at least about 80% sequence identity, at least about 85% sequence identity, and more preferably at least about 90%, 95% or even greater, such as 98% or 99% sequence identity with polynucleotide sequences described herein.

Protein and Polypeptide Molecules—This invention also provides polypeptides encoded by polynucleotides of the present invention. Amino acid sequences of the polypeptides of the present invention are provided herein as SEQ ID NOs: 9678-12046 and additionally in U.S. application Ser. No. 10/612,783 as SEQ ID NOs: 3550-7098, wherein SEQ ID NOs: 3550-4040 represent sequences derived from Glycine max, SEQ ID NOs: 4041-6574 represent sequences derived from Zea mays, and SEQ ID NOs: 6575-7098 represent sequences derived from Oryza sativa.

As used herein, the term "polypeptide" means an unbranched chain of amino acid residues that are covalently linked by an amide linkage between the carboxyl group of one amino acid and the amino group of another. The term polypeptide can encompass whole proteins (i.e. a functional protein encoded by a particular gene), as well as fragments of proteins. Of particular interest are polypeptides of the present invention which represent whole proteins or a sufficient portion of the entire protein to impart the relevant biological activity of the protein. The term "protein" also includes molecules consisting of one or more polypeptide chains. Thus, a polypeptide of the present invention may also constitute an entire gene product, but only a portion of a functional oligomeric protein having multiple polypeptide chains.

Of particular interest in the present invention are polypeptides involved in one or more important biological properties in plants. Such polypeptides may be produced in transgenic plants to provide plants having improved phenotypic properties and/or improved response to stressful environmental conditions. In some cases, decreased expression of such polypeptides may be desired, such decreased expression being obtained by use of the polynucleotide sequences provided herein, for example in antisense or cosuppression methods. See, e.g., Table 1 of U.S. application Ser. No. 10/612,783, and Table 2 and Table 3 of the present application for a list of improved plant properties and responses, and SEQ ID NOs: 9678-12046 for the polypeptides whose expression may be altered in transgenic plants to impart such improvements. A summary of such improved properties and polypeptides of interest for increased or decreased expression is provided below.

Yield/Nitrogen: Yield improvement by improved nitrogen flow, sensing, uptake, storage and/or transport. Polypeptides useful for imparting such properties include those involved in aspartate and glutamate biosynthesis, polypeptides involved in aspartate and glutamate transport, polypeptides associated with the TOR (Target of Rapamycin) pathway, nitrate transporters, ammonium transporters, chlorate transporters and polypeptides involved in tetrapyrrole biosynthesis.

Yield/Carbohydrate: Yield improvement by effects on carbohydrate metabolism, for example by increased sucrose production and/or transport. Polypeptides useful for improved yield by effects on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, and polypeptides involved in glucose signaling, such as SNF1 complex proteins.

Yield/Photosynthesis: Yield improvement resulting from increased photosynthesis. Polypeptides useful for increasing the rate of photosynthesis include phytochrome, photosystem I and II proteins, electron carriers, ATP synthase, NADH dehydrogenase and cytochrome oxidase.

Yield/Phosphorus: Yield improvement resulting from increased phosphorus uptake, transport or utilization. Polypeptides useful for improving yield in this manner include phosphatases and phosphate transporters.

Yield/Stress tolerance: Yield improvement resulting from improved plant growth and development by helping plants to tolerate stressful growth conditions. Polypeptides useful for improved stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in transgenic plants will provide changes in the ability of a plant to respond to a variety of environmental stresses, such as chemical stress, drought stress and pest stress.

Cold tolerance: Polypeptides of interest for improving plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins and uncoupling protein.

Heat tolerance: Polypeptides of interest for improving plant tolerance to heat include polypeptides involved in biosynthesis of trehalose, polypeptides involved in glycerolipid biosynthesis or membrane lipid metabolism (for altering membrane fatty acid composition), heat shock proteins and mitochondrial NDK.

Osmotic tolerance: Polypeptides of interest for improving plant tolerance to extreme osmotic conditions include polypeptides involved in proline biosynthesis.

Drought tolerance: Polypeptides of interest for improving plant tolerance to drought conditions include aquaporins, polypeptides involved in biosynthesis of trehalose or wax, LEA proteins and invertase.

Pathogen or pest tolerance: Polypeptides of interest for improving plant tolerance to effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects.

Cell cycle modification: Polypeptides encoding cell cycle enzymes and regulators of the cell cycle pathway are useful for manipulating growth rate in plants to provide early vigor and accelerated maturation leading to improved yield. Improvements in quality traits, such as seed oil content, may also be obtained by expression of cell cycle enzymes and cell cycle regulators. Polypeptides of interest for modification of cell cycle pathway include cyclins and EIF5alpha pathway proteins, polypeptides involved in polyamine metabolism, polypeptides which act as regulators of the cell cycle pathway, including cyclin-dependent kinases (CDKs), CDK-activating kinases, CDK-inhibitors, Rb and Rb-binding proteins, and transcription factors that activate genes involved in cell proliferation and division, such as the E2F family of transcription factors, proteins involved in degradation of cyclins, such as cullins, and plant homologs of tumor suppressor polypeptides.

Seed protein yield/content: Polypeptides useful for providing increased seed protein quantity and/or quality include polypeptides involved in the metabolism of amino acids in plants, particularly polypeptides involved in biosynthesis of methionine/cysteine and lysine, amino acid transporters, amino acid efflux carriers, seed storage proteins, proteases, and polypeptides involved in phytic acid metabolism.

Seed oil yield/content: Polypeptides useful for providing increased seed oil quantity and/or quality include polypeptides involved in fatty acid and glycerolipid biosynthesis, beta-oxidation enzymes, enzymes involved in biosynthesis of nutritional compounds, such as carotenoids and tocopherols, and polypeptides that increase embryo size or number or thickness of aleurone.

Disease response in plants: Polypeptides useful for imparting improved disease responses to plants include polypeptides encoded by cercosporin induced genes, antifungal proteins and proteins encoded by R-genes or SAR genes. Expression of such polypeptides in transgenic plants will provide an increase in disease resistance ability of plants.

Galactomannanan biosynthesis: Polypeptides involved in production of galactomannans are of interest for providing plants having increased and/or modified reserve polysaccharides for use in food, pharmaceutical, cosmetic, paper and paint industries.

Flavonoid/isoflavonoid metabolism in plants: Polypeptides of interest for modification of flavonoid/isoflavonoid metabolism in plants include cinnamate-4-hydroxylase, chalcone synthase and flavonol synthase. Enhanced or reduced activity of such polypeptides in transgenic plants will provide changes in the quantity and/or speed of flavonoid metabolism in plants and may improve disease resistance by enhancing synthesis of protective secondary metabolites or improving signaling pathways governing disease resistance.

Plant growth regulators: Polypeptides involved in production of substances that regulate the growth of various plant tissues are of interest in the present invention and may be used to provide transgenic plants having altered morphologies and improved plant growth and development profiles leading to improvements in yield and stress response. Of particular interest are polypeptides involved in the biosynthesis of plant growth hormones, such as gibberellins, cytokinins, auxins, ethylene and abscisic acid, and other proteins involved in the activity and/or transport of such polypeptides, including for example, cytokinin oxidase, cytokinin/purine permeases, F-box proteins, G-proteins and phytosulfokines.

Herbicide tolerance: Polypeptides of interest for producing plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

Transcription factors in plants: Transcription factors play a key role in plant growth and development by controlling the expression of one or more genes in temporal, spatial and physiological specific patterns. Enhanced or reduced activity of such polypeptides in transgenic plants will provide significant changes in gene transcription patterns and provide a variety of beneficial effects in plant growth, development and response to environmental conditions. Transcription factors of interest include, but are not limited to myb transcription factors, including helix-turn-helix proteins, homeodomain transcription factors, leucine zipper transcription factors, MADS transcription factors, transcription factors having AP2 domains, zinc finger transcription factors, CCAAT binding transcription factors, ethylene responsive transcription factors, transcription initiation factors and UV damaged DNA binding proteins.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, including for example, resolvases and polypeptide members of the RAD52 epistasis group.

Lignin biosynthesis: Polypeptides involved in lignin biosynthesis are of interest for increasing plants' resistance to lodging and for increasing the usefulness of plant materials as biofuels.

The function of polypeptides of the present invention is determined by comparison of the amino acid sequence of the novel polypeptides to amino acid sequences of known polypeptides. A variety of homology based search algorithms are available to compare a query sequence to a protein database, including for example, BLAST, FASTA, and Smith-Waterman. In the present application, BLASTX and BLASTP algorithms are used to provide protein function information. A number of values are examined in order to assess the confidence of the function assignment. Useful measurements include "E-value" (also shown as "hit_p"), "percent identity", "percent query coverage", and "percent hit coverage".

In BLAST, E-value, or expectation value, represents the number of different alignments with scores equivalent to or better than the raw alignment score, S, that are expected to occur in a database search by chance. The lower the E value, the more significant the match. Because database size is an element in E-value calculations, E-values obtained by BLASTing against public databases, such as GenBank, have generally increased over time for any given query/entry match. In setting criteria for confidence of polypeptide function prediction, a "high" BLAST match is considered herein as having an E-value for the top BLAST hit provided in Table 1 of U.S. application Ser. No. 10/612,783 and Table 2 of the present application of less than 1E-30; a medium BLASTX E-value is 1E-30 to 1E-8; and a low BLASTX E-value is greater than 1E-8. The top BLAST hit and corresponding E values are provided in Table 1 of U.S. application Ser. No. 10/612,783 and Table 2 of the present application.

Percent identity refers to the percentage of identically matched amino acid residues that exist along the length of that portion of the sequences which is aligned by the BLAST algorithm. In setting criteria for confidence of polypeptide function prediction, a "high" BLAST match is considered herein as having percent identity for the top BLAST hit provided in Table 1 of U.S. application Ser. No. 10/612,783 and Table 2 of the present application of at least 70%; a medium percent identity value is 35% to 70%; and a low percent identity is less than 35%.

Of particular interest in protein function assignment in the present invention is the use of combinations of E-values, percent identity, query coverage and hit coverage. Query coverage refers to the percent of the query sequence that is represented in the BLAST alignment. Hit coverage refers to the percent of the database entry that is represented in the BLAST alignment. In the present invention, function of a query polypeptide is inferred from function of a protein homolog where either (1) hit_p<1e-30 or % identity>35% AND query_coverage>50% AND hit_coverage>50%, or (2) hit_p<1e-8 AND query_coverage>70% AND hit_coverage>70%.

A further aspect of the invention comprises functional homologs which differ in one or more amino acids from those of a polypeptide provided herein as the result of one or more conservative amino acid substitutions. It is well known in the art that one or more amino acids in a native sequence can be substituted with at least one other amino acid, the charge and polarity of which are similar to that of the native amino acid, resulting in a silent change. For instance, valine is a conservative substitute for alanine and threonine is a conservative substitute for serine. Conservative substitutions for an amino acid within the native polypeptide sequence can be selected from other members of the class to which the naturally occurring amino acid belongs. Amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention comprises polypeptides which differ in one or more amino acids from those of a soy protein sequence as the result of deletion or insertion of one or more amino acids in a native sequence.

Also of interest in the present invention are functional homologs of the polypeptides provided herein which have the same function as a polypeptide provided herein, but with increased or decreased activity or altered specificity. Such variations in protein activity may exist naturally in polypeptides encoded by related genes, for example in a related polypeptide encodes by a different allele or in a different species, or can be achieved by mutagenesis. Naturally occurring variant polypeptides may be obtained by well known nucleic acid or protein screening methods using DNA or antibody probes, for example by screening libraries for genes encoding related polypeptides, or in the case of expression libraries, by screening directly for variant polypeptides. Screening methods for obtaining a modified protein or enzymatic activity of interest by mutagenesis are disclosed in U.S. Pat. No. 5,939,250. An alternative approach to the generation of variants uses random recombination techniques such as "DNA shuffling" as disclosed in U.S. Pat. Nos. 5,605,793; 5,811,238; 5,830,721 and 5,837,458; and International Applications WO 98/31837 and WO 99/65927, all of which are incorporated herein by reference. An alternative method of molecular evolution involves a staggered extension process (StEP) for in vitro mutagenesis and recombination of nucleic acid molecule sequences, as disclosed in U.S. Pat. No. 5,965,408 and International Application WO 98/42832, both of which are incorporated herein by reference.

Polypeptides of the present invention that are variants of the polypeptides provided herein will generally demonstrate significant identity with the polypeptides provided herein. Of particular interest are polypeptides having at least about 35% sequence identity, at least about 50% sequence identity, at least about 60% sequence identity, at least about 70% sequence identity, at least about 80% sequence identity, and more preferably at least about 85%, 90%, 95% or even greater, sequence identity with polypeptide sequences described herein. Of particular interest in the present invention are polypeptides having amino acid sequences provided herein (reference polypeptides) and functional homologs of such reference polypeptides, wherein such functional homologs comprises at least 50 consecutive amino acids having at least 90% identity to a 50 amino acid polypeptide fragment of said reference polypeptide.

Recombinant DNA Constructs—The present invention also encompasses the use of polynucleotides of the present invention in recombinant constructs, i.e. constructs comprising polynucleotides that are constructed or modified outside of cells and that join nucleic acids that are not found joined in nature. Using methods known to those of ordinary skill in the art, polypeptide encoding sequences of this invention can be inserted into recombinant DNA constructs that can be introduced into a host cell of choice for expression of the encoded protein, or to provide for reduction of expression of the encoded protein, for example by antisense or cosuppression methods. Potential host cells include both prokaryotic and eukaryotic cells. Of particular interest in the present invention is the use of the polynucleotides of the present invention for preparation of constructs for use in plant transformation.

In plant transformation, exogenous genetic material is transferred into a plant cell. By "exogenous" it is meant that a nucleic acid molecule, for example a recombinant DNA construct comprising a polynucleotide of the present invention, is produced outside the organism, e.g. plant, into which it is introduced. An exogenous nucleic acid molecule can have a naturally occurring or non-naturally occurring nucleotide sequence. One skilled in the art recognizes that an exogenous nucleic acid molecule can be derived from the same species into which it is introduced or from a different species. Such exogenous genetic material may be transferred into either monocot or dicot plants including, but not limited to, soy, cotton, canola, maize, teosinte, wheat, rice and *Arabidopsis* plants. Transformed plant cells comprising such exogenous genetic material may be regenerated to produce whole transformed plants.

Exogenous genetic material may be transferred into a plant cell by the use of a DNA vector or construct designed for such a purpose. A construct can comprise a number of sequence elements, including promoters, encoding regions, and selectable markers. Vectors are available which have been designed to replicate in both *E. coli* and *A. tumefaciens* and have all of the features required for transferring large inserts of DNA into plant chromosomes. Design of such vectors is generally within the skill of the art.

A construct will generally include a plant promoter to direct transcription of the protein-encoding region or the antisense sequence of choice. Numerous promoters, which are active in plant cells, have been described in the literature. These include the nopaline synthase (NOS) promoter and octopine synthase (OCS) promoters carried on tumor-inducing plasmids of *Agrobacterium tumefaciens* or caulimovirus promoters such as the Cauliflower Mosaic Virus (CaMV) 19S or 35S promoter (U.S. Pat. No. 5,352,605), and the Figwort Mosaic Virus (FMV) 35S-promoter (U.S. Pat. No. 5,378, 619). These promoters and numerous others have been used to create recombinant vectors for expression in plants. Any promoter known or found to cause transcription of DNA in plant cells can be used in the present invention. Other useful promoters are described, for example, in U.S. Pat. Nos. 5,378, 619; 5,391,725; 5,428,147; 5,447,858; 5,608,144; 5,614,399; 5,633,441; and 5,633,435, all of which are incorporated herein by reference.

In addition, promoter enhancers, such as the CaMV 35S enhancer or a tissue specific enhancer, may be used to enhance gene transcription levels. Enhancers often are found 5' to the start of transcription in a promoter that functions in eukaryotic cells, but can often be inserted in the forward or reverse orientation 5' or 3' to the coding sequence. In some instances, these 5' enhancing elements are introns. Deemed to be particularly useful as enhancers are the 5' introns of the rice actin 1 and rice actin 2 genes. Examples of other enhancers which could be used in accordance with the invention include elements from octopine synthase genes, the maize alcohol dehydrogenase gene intron 1, elements from the maize shrunken 1 gene, the sucrose synthase intron, the TMV omega element, and promoters from non-plant eukaryotes.

DNA constructs can also contain one or more 5' non-translated leader sequences which serve to enhance polypeptide production from the resulting mRNA transcripts. Such sequences may be derived from the promoter selected to express the gene or can be specifically modified to increase translation of the mRNA. Such regions may also be obtained from viral RNAs, from suitable eukaryotic genes, or from a synthetic gene sequence. For a review of optimizing expression of transgenes, see Koziel et al. (1996) Plant Mol. Biol. 32:393-405).

Constructs and vectors may also include, with the coding region of interest, a nucleic acid sequence that acts, in whole or in part, to terminate transcription of that region. One type of 3' untranslated sequence which may be used is a 3' UTR from the nopaline synthase gene (nos 3') of Agrobacterium tumefaciens. Other 3' termination regions of interest include those from a gene encoding the small subunit of a ribulose-1,5-bisphosphate carboxylase-oxygenase (rbcS), and more specifically, from a rice rbcS gene (U.S. Pat. No. 6,426,446), the 3' UTR for the T7 transcript of Agrobacterium tumefaciens, the 3' end of the protease inhibitor I or II genes from potato or tomato, and the 3' region isolated from Cauliflower Mosaic Virus. Alternatively, one also could use a gamma coixin, oleosin 3 or other 3' UTRs from the genus Coix (PCT Publication WO 99/58659).

Constructs and vectors may also include a selectable marker. Selectable markers may be used to select for plants or plant cells that contain the exogenous genetic material. Useful selectable marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable markers are illustrated in U.S. Pat. Nos. 5,550,318; 5,633,435; 5,780,708 and 6,118,047, all of which are incorporated herein by reference.

Constructs and vectors may also include a screenable marker. Screenable markers may be used to monitor transformation. Exemplary screenable markers include genes expressing a colored or fluorescent protein such as a luciferase or green fluorescent protein (GFP), a β-glucuronidase or uidA gene (GUS) which encodes an enzyme for which various chromogenic substrates are known or an R-locus gene, which encodes a product that regulates the production of anthocyanin pigments (red color) in plant tissues. Other possible selectable and/or screenable marker genes will be apparent to those of skill in the art.

Constructs and vectors may also include a transit peptide for targeting of a gene target to a plant organelle, particularly to a chloroplast, leucoplast or other plastid organelle (U.S. Pat. No. 5,188,642).

For use in Agrobacterium mediated transformation methods, constructs of the present invention will also include T-DNA border regions flanking the DNA to be inserted into the plant genome to provide for transfer of the DNA into the plant host chromosome as discussed in more detail below. An exemplary plasmid that finds use in such transformation methods is pMON18365, a T-DNA vector that can be used to clone exogenous genes and transfer them into plants using Agrobacterium-mediated transformation. See US Patent Application 20030024014, herein incorporated by reference. This vector contains the left border and right border sequences necessary for Agrobacterium transformation. The plasmid also has origins of replication for maintaining the plasmid in both E. coli and Agrobacterium tumefaciens strains.

A candidate gene is prepared for insertion into the T-DNA vector, for example using well-known gene cloning techniques such as PCR. Restriction sites may be introduced onto each end of the gene to facilitate cloning. For example, candidate genes may be amplified by PCR techniques using a set of primers. Both the amplified DNA and the cloning vector are cut with the same restriction enzymes, for example, NotI and PstI. The resulting fragments are gel-purified, ligated together, and transformed into E. coli. Plasmid DNA containing the vector with inserted gene may be isolated from E. coli cells selected for spectinomycin resistance, and the presence of the desired insert verified by digestion with the appropriate restriction enzymes. Undigested plasmid may then be transformed into Agrobacterium tumefaciens using techniques well known to those in the art, and transformed Agrobacterium cells containing the vector of interest selected based on spectinomycin resistance. These and other similar constructs useful for plant transformation may be readily prepared by one skilled in the art.

Transformation Methods and Transgenic Plants—Methods and compositions for transforming bacteria and other microorganisms are known in the art. See for example Molecular Cloning: A Laboratory Manual, $3^{rd}$ edition Volumes 1, 2, and 3. J. F. Sambrook, D. W. Russell, and N. Irwin, Cold Spring Harbor Laboratory Press, 2000.

Technology for introduction of DNA into cells is well known to those of skill in the art. Methods and materials for transforming plants by introducing a transgenic DNA construct into a plant genome in the practice of this invention can include any of the well-known and demonstrated methods including electroporation as illustrated in U.S. Pat. No. 5,384,253, microprojectile bombardment as illustrated in U.S. Pat. Nos. 5,015,580; 5,550,318; 5,538,880; 6,160,208; 6,399,861 and 6,403,865, Agrobacterium-mediated transformation as illustrated in U.S. Pat. Nos. 5,635,055; 5,824,877; 5,591,616; 5,981,840 and 6,384,301, and protoplast transformation as illustrated in U.S. Pat. No. 5,508,184, all of which are incorporated herein by reference.

Any of the polynucleotides of the present invention may be introduced into a plant cell in a permanent or transient manner in combination with other genetic elements such as vectors, promoters enhancers etc. Further any of the polynucleotides of the present invention may be introduced into a plant cell in a manner that allows for production of the polypeptide or fragment thereof encoded by the polynucleotide in the plant cell, or in a manner that provides for decreased expression of an endogenous gene and concomitant decreased production of protein.

It is also to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated, as is vegetative propagation.

Expression of the polynucleotides of the present invention and the concomitant production of polypeptides encoded by the polynucleotides is of interest for production of transgenic plants having improved properties, particularly, improved properties which result in crop plant yield improvement. Expression of polypeptides of the present invention in plant cells may be evaluated by specifically identifying the protein products of the introduced genes or evaluating the phenotypic changes brought about by their expression. It is noted that when the polypeptide being produced in a transgenic plant is native to the target plant species, quantitative analyses comparing the transformed plant to wild type plants may be required to demonstrate increased expression of the polypeptide of this invention.

Assays for the production and identification of specific proteins make use of various physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, particularly where the expressed protein is an enzyme capable of catalyzing chemical reactions involving specific substrates and products. These reactions may be measured, for example in plant extracts, by providing and quantifying the loss of substrates or the generation of products of the reactions by physical and/or chemical procedures.

In many cases, the expression of a gene product is determined by evaluating the phenotypic results of its expression. Such evaluations may be simply as visual observations, or may involve assays. Such assays may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks.

Plants with decreased expression of a gene of interest can also be achieved through the use of polynucleotides of the present invention, for example by expression of antisense nucleic acids, or by identification of plants transformed with sense expression constructs that exhibit cosuppression effects.

Antisense approaches are a way of preventing or reducing gene function by targeting the genetic material as disclosed in U.S. Pat. Nos. 4,801,540; 5,107,065; 5,759,829; 5,910,444; 6,184,439; and 6,198,026, all of which are incorporated herein by reference. The objective of the antisense approach is to use a sequence complementary to the target gene to block its expression and create a mutant cell line or organism in which the level of a single chosen protein is selectively reduced or abolished. Antisense techniques have several advantages over other 'reverse genetic' approaches. The site of inactivation and its developmental effect can be manipulated by the choice of promoter for antisense genes or by the timing of external application or microinjection. Antisense can manipulate its specificity by selecting either unique regions of the target gene or regions where it shares homology to other related genes.

The principle of regulation by antisense RNA is that RNA that is complementary to the target mRNA is introduced into cells, resulting in specific RNA:RNA duplexes being formed by base pairing between the antisense substrate and the target. Under one embodiment, the process involves the introduction and expression of an antisense gene sequence. Such a sequence is one in which part or all of the normal gene sequences are placed under a promoter in inverted orientation so that the 'wrong' or complementary strand is transcribed into a noncoding antisense RNA that hybridizes with the target mRNA and interferes with its expression. An antisense vector is constructed by standard procedures and introduced into cells by transformation, transfection, electroporation, microinjection, infection, etc. The type of transformation and choice of vector will determine whether expression is transient or stable. The promoter used for the antisense gene may influence the level, timing, tissue, specificity, or inducibility of the antisense inhibition.

As used herein "gene suppression" means any of the well-known methods for suppressing expression of protein from a gene including sense suppression, anti-sense suppression and RNAi suppression. In suppressing genes to provide plants with a desirable phenotype, anti-sense and RNAi gene suppression methods are preferred. More particularly, for a description of anti-sense regulation of gene expression in plant cells see U.S. Pat. No. 5,107,065 and for a description of RNAi gene suppression in plants by transcription of a dsRNA see U.S. Pat. No. 6,506,559, U.S. Patent Application Publication No. 2002/0168707 A1, and U.S. patent application Ser. Nos. 09/423,143 (see WO 98/53083), 09/127,735 (see WO 99/53050) and 09/084,942 (see WO 99/61631), all of which are incorporated herein by reference. Suppression of an gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure. For example, genomic DNA from a polymorphic locus of SEQ ID NOs: 1-9677 can be used in a recombinant construct for suppression of a cognate gene by RNAi suppression.

Insertion mutations created by transposable elements may also prevent gene function. For example, in many dicot plants, transformation with the T-DNA of *Agrobacterium* may be readily achieved and large numbers of transformants can be rapidly obtained. Also, some species have lines with active transposable elements that can efficiently be used for the generation of large numbers of insertion mutations, while some other species lack such options. Mutant plants produced by *Agrobacterium* or transposon mutagenesis and having altered expression of a polypeptide of interest can be identified using the polynucleotides of the present invention. For example, a large population of mutated plants may be screened with polynucleotides encoding the polypeptide of interest to detect mutated plants having an insertion in the gene encoding the polypeptide of interest.

Polynucleotides of the present invention may be used in site-directed mutagenesis. Site-directed mutagenesis may be utilized to modify nucleic acid sequences, particularly as it is a technique that allows one or more of the amino acids encoded by a nucleic acid molecule to be altered (e.g., a threonine to be replaced by a methionine). Three basic methods for site-directed mutagenesis are often employed. These are cassette mutagenesis, primer extension, and methods based upon PCR.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones.

Arrays—The polynucleotide or polypeptide molecules of this invention may also be used to prepare arrays of target molecules arranged on a surface of a substrate. The target molecules are preferably known molecules, e.g. polynucleotides (including oligonucleotides) or polypeptides, which are capable of binding to specific probes, such as complementary nucleic acids or specific antibodies. The target molecules are preferably immobilized, e.g. by covalent or non-covalent bonding, to the surface in small amounts of substantially purified and isolated molecules in a grid pattern. By immobilized is meant that the target molecules maintain their position relative to the solid support under hybridization and washing conditions. Target molecules are deposited in small footprint, isolated quantities of "spotted elements" of preferably single-stranded polynucleotide preferably arranged in rectangular grids in a density of about 30 to 100 or more, e.g. up to about 1000, spotted elements per square centimeter. In addition in preferred embodiments arrays comprise at least about 100 or more, e.g. at least about 1000 to 5000, distinct target polynucleotides per unit substrate. Where detection of transcription for a large number of genes is desired, the economics of arrays favors a high density design criteria provided that the target molecules are sufficiently separated so that the intensity of the indicia of a binding event associated with highly expressed probe molecules does not overwhelm and mask the indicia of neighboring binding events. For high-density microarrays each spotted element may contain up to about $10^7$ or more copies of the target molecule, e.g. single stranded cDNA, on glass substrates or nylon substrates.

Arrays of this invention can be prepared with molecules from a single species, preferably a plant species, or with molecules from other species, particularly other plant species. Arrays with target molecules from a single species can be used with probe molecules from the same species or a different species due to the ability of cross species homologous genes to hybridize. It is generally preferred for high stringency hybridization that the target and probe molecules are from the same species.

In preferred aspects of this invention the organism of interest is a plant and the target molecules are polynucleotides or oligonucleotides with nucleic acid sequences having at least 80 percent sequence identity to a corresponding sequence of the same length in a polynucleotide having a sequence selected from the group consisting of SEQ ID NOs: 1-9677 or complements thereof. In other preferred aspects of the invention at least 10% of the target molecules on an array have at least 15, more preferably at least 20, consecutive nucleotides of sequence having at least 80%, more preferably up to 100%, identity with a corresponding sequence of the same length in a polynucleotide having a sequence selected from the group consisting of SEQ ID NOs: 1-9677 or complements or fragments thereof.

Such arrays are useful in a variety of applications, including gene discovery, genomic research, molecular breeding and bioactive compound screening. One important use of arrays is in the analysis of differential gene transcription, e.g. transcription profiling where the production of mRNA in different cells, normally a cell of interest and a control, is compared and discrepancies in gene expression are identified. In such assays, the presence of discrepancies indicates a difference in gene expression levels in the cells being compared. Such information is useful for the identification of the types of genes expressed in a particular cell or tissue type in a known environment. Such applications generally involve the following steps: (a) preparation of probe, e.g. attaching a label to a plurality of expressed molecules; (b) contact of probe with the array under conditions sufficient for probe to bind with corresponding target, e.g. by hybridization or specific binding; (c) removal of unbound probe from the array; and (d) detection of bound probe.

A probe may be prepared with RNA extracted from a given cell line or tissue. The probe may be produced by reverse transcription of mRNA or total RNA and labeled with radioactive or fluorescent labeling. A probe is typically a mixture containing many different sequences in various amounts, corresponding to the numbers of copies of the original mRNA species extracted from the sample.

The initial RNA sample for probe preparation will typically be derived from a physiological source. The physiological source may be selected from a variety of organisms, with physiological sources of interest including single celled organisms such as yeast and multicellular organisms, including plants and animals, particularly plants, where the physiological sources from multicellular organisms may be derived from particular organs or tissues of the multicellular organism, or from isolated cells derived from an organ, or tissue of the organism. The physiological sources may also be multicellular organisms at different developmental stages (e.g., 10-day-old seedlings), or organisms grown under different environmental conditions (e.g., drought-stressed plants) or treated with chemicals.

In preparing the RNA probe, the physiological source may be subjected to a number of different processing steps, where such processing steps might include tissue homogenation, cell isolation and cytoplasmic extraction, nucleic acid extraction and the like, where such processing steps are known to the those of skill in the art. Methods of isolating RNA from cells, tissues, organs or whole organisms are known to those of skill in the art.

Computer Based Systems and Methods—The sequence of the molecules of this invention can be provided in a variety of media to facilitate use thereof. Such media can also provide a subset thereof in a form that allows a skilled artisan to examine the sequences. In a preferred embodiment, 20, preferably 50, more preferably 100, even more preferably 200 or more of the polynucleotide and/or the polypeptide sequences of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; and hybrids of these categories such as magnetic/optical storage media. A skilled artisan can readily appreciate how any of the presently known computer readable media can be used to create a manufacture comprising a computer readable medium having recorded thereon a nucleotide sequence of the present invention.

As used herein, "recorded" refers to a process for storing information on computer readable media. A skilled artisan can readily adopt any of the presently known methods for recording information on computer readable media to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable media. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g., text file or database) in order to obtain a computer readable medium having recorded thereon the nucleotide sequence information of the present invention.

By providing one or more of polynucleotide or polypeptide sequences of the present invention in a computer readable medium, a skilled artisan can routinely access the sequence information for a variety of purposes. The examples which follow demonstrate how software which implements the BLAST and BLAZE search algorithms on a Sybase system can be used to identify open reading frames (ORFs) within the genome that contain homology to ORFs or polypeptides from other organisms. Such ORFs are polypeptide encoding fragments within the sequences of the present invention and are useful in producing commercially important polypeptides such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware, software, and memory used to analyze the sequence information of the present invention. A skilled artisan can readily appreciate that any one of the currently available computer-based systems are suitable for use in the present invention.

As indicated above, the computer-based systems of the present invention comprise a database having stored therein a nucleotide sequence of the present invention and the necessary hardware and software for supporting and implementing a homology search. As used herein, "database" refers to memory system that can store searchable nucleotide sequence information. As used herein "query sequence" is a nucleic acid sequence, or an amino acid sequence, or a nucleic acid sequence corresponding to an amino acid sequence, or an amino acid sequence corresponding to a nucleic acid sequence, that is used to query a collection of nucleic acid or amino acid sequences. As used herein, "homology search" refers to one or more programs which are implemented on the computer-based system to compare a query sequence, i.e., gene or peptide or a conserved region (motif), with the sequence information stored within the database. Homology searches are used to identify segments and/or regions of the sequence of the present invention that match a particular query sequence. A variety of known searching algorithms are incorporated into commercially available software for conducting homology searches of databases and computer readable media comprising sequences of molecules of the present invention.

Commonly preferred sequence length of a query sequence is from about 10 to 100 or more amino acids or from about 20 to 300 or more nucleotide residues. There are a variety of motifs known in the art. Protein motifs include, but are not limited to, enzymatic active sites and signal sequences. An amino acid query is converted to all of the nucleic acid sequences that encode that amino acid sequence by a software program, such as TBLASTN, which is then used to search the database. Nucleic acid query sequences that are motifs include, but are not limited to, promoter sequences, cis elements, hairpin structures and inducible expression elements (protein binding sequences).

Thus, the present invention further provides an input device for receiving a query sequence, a memory for storing sequences (the query sequences of the present invention and sequences identified using a homology search as described above) and an output device for outputting the identified homologous sequences. A variety of structural formats for the input and output presentations can be used to input and output information in the computer-based systems of the present invention. A preferred format for an output presentation ranks fragments of the sequence of the present invention by varying degrees of homology to the query sequence. Such presentation provides a skilled artisan with a ranking of sequences that contain various amounts of the query sequence and identifies the degree of homology contained in the identified fragment.

Having now generally described the invention, the same will be more readily understood through reference to the following examples which are provided by way of illustration, and are not intended to be limiting of the present invention, unless specified.

EXAMPLE 1

A cDNA library is generated from *Zea mays*, *Oryza sativa*, or *Glycine max* tissue. Tissue is harvested and immediately frozen in liquid nitrogen. The harvested tissue is stored at −80° C. until preparation of total RNA. The total RNA is purified using Trizol reagent from Invitrogen Corporation (Invitrogen Corporation, Carlsbad, Calif., U.S.A.), essentially as recommended by the manufacturer. Poly A+ RNA (mRNA) is purified using magnetic oligo dT beads essentially as recommended by the manufacturer (Dynabeads, Dynal Biotech, Oslow, Norway).

Construction of plant cDNA libraries is well known in the art and a number of cloning strategies exist. A number of cDNA library construction kits are commercially available cDNA libraries are prepared using the Superscript™ Plasmid System for cDNA synthesis and Plasmid Cloning (Invitrogen Corporation, Carlsbad, Calif., U.S.A.), as described in the Superscript II cDNA library synthesis protocol. The cDNA libraries are quality controlled for a good insert:vector ratio.

The cDNA libraries are plated on LB agar containing the appropriate antibiotics for selection and incubated at 37° for a sufficient time to allow the growth of individual colonies. Single colonies are individually placed in each well of a 96-well microtiter plates containing LB liquid including the selective antibiotics. The plates are incubated overnight at approximately 37° C. with gentle shaking to promote growth of the cultures. The plasmid DNA is isolated from each clone using Qiaprep plasmid isolation kits, using the conditions recommended by the manufacturer (Qiagen Inc., Valencia, Calif. U.S.A.).

The template plasmid DNA clones are used for subsequent sequencing. Sequences of polynucleotides may be obtained by a number of sequencing techniques known in the art, including fluorescence-based sequencing methodologies.

These methods have the detection, automation, and instrumentation capability necessary for the analysis of large volumes of sequence data. With these types of automated systems, fluorescent dye-labeled sequence reaction products are detected and data entered directly into the computer, producing a chromatogram that is subsequently viewed, stored, and analyzed using the corresponding software programs. These methods are known to those of skill in the art and have been described and reviewed.

EXAMPLE 2

The open reading frame in each polynucleotide sequence is identified by a combination of predictive and homology based methods. The longest open reading frame (ORF) is determined, and the top BLAST match is identified by BLASTX against NCBI. The top BLAST hit is then compared to the predicted ORF, with the BLAST hit given precedence in the case of discrepancies.

Functions of polypeptides encoded by the polynucleotide sequences of the present invention are determined using a hierarchical classification tool, termed FunCAT, for Functional Categories Annotation Tool. Most categories collected in FunCAT are classified by function, although other criteria are used, for example, cellular localization or temporal process. The assignment of a functional category to a query sequence is based on BLASTX sequence search results, which compare two protein sequences. FunCAT assigns categories by iteratively scanning through all blast hits, starting with the most significant match, and reporting the first category assignment for each FunCAT source classification scheme. In the present invention, function of a query polypeptide is inferred from the function of a protein homolog where either (1) hit_p<1e-30 or % identity>35% AND query_coverage>50% AND hit_coverage>50%, or (2) hit_p<1 e-8 AND query_coverage>70% AND hit_coverage>70%.

Functional assignments from five public classification schemes, GO_BP, GO_CC, GO_MF, KEGG, and EC, and one internal Monsanto classification scheme, POI, are provided in Table 1 of U.S. application Ser. No. 10/612,783 and Table 2 of the present application. The column under the heading "CAT_TYPE" indicates the source of the classification. GO_BP=Gene Ontology Consortium–biological process; GO_CC=Gene Ontology Consortium–cellular component; GO_MF=Gene Ontology Consortium–molecular function; KEGG=KEGG functional hierarchy; EC=Enzyme Classification from ENZYME data bank release 25.0; POI=Pathways of Interest. The column under the heading "CAT_DESC" provides the name of the subcategory into which the query sequence was classified. The column under the heading "PRODUCT_HIT_DESC" provides a description of the BLAST hit to the query sequences that led to the specific classification. The column under the heading "HIT_E" provides the e-value for the BLAST hit. It is noted that the e-value in the HIT_E column may differ from the e-value based on the top BLAST hit provided in the E_VALUE column since these calculations were done on different days, and database size is an element in E-value calculations. E-values obtained by BLASTing against public databases, such as GenBank, will generally increase over time for any given query/entry match.

Sequences useful for producing transgenic plants having improved biological properties are identified from their FunCAT annotations and are also provided in Table 1 of U.S. application Ser. No. 10/612,783. A biological property of particular interest is plant yield. Plant yield may be improved by alteration of a variety of plant pathways, including those involving nitrogen, carbohydrate, or phosphorus utilization and/or uptake. Plant yield may also be improved by alteration of a plant's photosynthetic capacity or by improving a plant's ability to tolerate a variety of environmental stresses, including cold, heat, drought and osmotic stresses. Other biological properties of interest that may be improved using sequences of the present invention include pathogen or pest tolerance, herbicide tolerance, disease resistance, growth rate (for example by modification of cell cycle, by expression of transcription factors, or expression of growth regulators), seed oil and/or protein yield and quality, rate and control of recombination, and lignin content.

Polynucleotide sequences are provided herein as SEQ ID NOs: 1-9677, and the translated polypeptide sequences for these polynucleotide sequences are provided as SEQ ID NOs: 9678-12046. Descriptions of each of these polynucleotide and polypeptide sequences are provided in Table 1 of U.S. application Ser. No. 10/612,783, and in Table 2 and Table 3 of the present application. The polynucleotide sequences of Table 1 of U.S. application Ser. No. 10/612,783 correspond to the SEQ ID NOs provided in the sequence listing filed in U.S. application Ser. No. 10/612,783. The polynucleotide sequences of Table 2 and Table 3 correspond to the SEQ ID NOs provided in the sequence listing of the present application.

Table 1 and Table 2 Column Descriptions

SEQ_NUM provides the SEQ ID NOs for the listed polynucleotide sequences.

CONTIG_ID provides an arbitrary sequence name taken from the name of the clone from which the cDNA sequence was obtained.

PROTEIN_NUM or PEP_NUM provides the SEQ ID NOs for the translated polypeptide sequence NCBI_GI provides the GenBank ID number for the top BLAST hit for the sequence. The top BLAST hit is indicated by the National Center for Biotechnology Information GenBank Identifier number.

SPECIES provides the name of the species from which the sequence was isolated.

NCBI_GI_DESCRIPTION refers to the description of the GenBank top BLAST hit for the sequence.

E_VALUE provides the expectation value for the top BLAST match.

MATCH_LENGTH provides the length of the sequence which is aligned in the top BLAST match TOP_HIT_PCT_IDENT/% IDENTITY refers to the percentage of identically matched nucleotides (or residues) that exist along the length of that portion of the sequences which is aligned in the top BLAST match.

CAT_TYPE indicates the classification scheme used to classify the sequence. GO_BP=Gene Ontology Consortium–biological process; GO_CC=Gene Ontology Consortium–cellular component; GO_MF=Gene Ontology Consortium–molecular function; KEGG=KEGG functional hierarchy (KEGG=Kyoto Encyclopedia of Genes and Genomes); EC=Enzyme Classification from ENZYME data bank release 25.0; POI=Pathways of Interest.

CAT_DESC provides the classification scheme subcategory to which the query sequence was assigned.

PRODUCT_CAT_DESC provides the FunCAT annotation category to which the query sequence was assigned.

PRODUCT_HIT_DESC provides the description of the BLAST hit which resulted in assignment of the sequence to the function category provided in the cat_desc column.

HIT_E/HIT_P provides the E value for the BLAST hit in the hit_desc column.

PCT_IDENT refers to the percentage of identically matched nucleotides (or residues) that exist along the length of that portion of the sequences which is aligned in the BLAST match provided in hit_desc.

QRY_RANGE lists the range of the query sequence aligned with the hit.

HIT_RANGE lists the range of the hit sequence aligned with the query.

QRY_CVRG provides the percent of query sequence length that matches to the hit (NCBI) sequence in the BLAST match (% qry cvrg=(match length/query total length)× 100).

HIT_CVRG provides the percent of hit sequence length that matches to the query sequence in the match generated using BLAST (% hit cvrg=(match length/hit total length)× 100).

All publications and patent applications cited herein are incorporated by reference in their entirely to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08299321B2). An electronic copy of the "Sequence Listing" will also be available from the USPTO upon request and payment of the fee set forth in 37 CFR 1.19(b)(3).

What is claimed is:

1. A transformed plant having a nucleic acid molecule which comprises:
   (a) an exogenous promoter region which functions in a plant cell to cause the production of an mRNA molecule, which is operably linked to
   (b) a structural nucleic acid molecule, wherein said structural nucleic acid molecule comprises a nucleic acid sequence, wherein said nucleic acid sequence encodes a polypeptide that has at least 95% sequence identity with the amino acid sequence of SEQ ID NO: 5111 and has deoxyhypusine synthase activity, which is operably linked to
   (c) a 3' non-translated sequence that functions in said plant cell to cause the termination of transcription and the addition of polyadenylated ribonucleotides to said 3' end of said mRNA molecule.

2. The transformed plant according to claim 1, wherein said plant is selected from the group consisting of soybean, maize, cotton and wheat.

3. A transformed seed comprising a transformed plant cell comprising a nucleic acid molecule which comprises:
   (a) an exogenous promoter region which functions in said plant cell to cause the production of an mRNA molecule, which is operably linked to
   (b) a structural nucleic acid molecule, wherein said structural nucleic acid molecule comprises a nucleic acid sequence, wherein said nucleic acid sequence encodes a polypeptide that has at least 95% sequence identity with the amino acid sequence of SEQ ID NO: 5111 and has deoxyhypusine synthase activity, which is operably linked to
   (c) a 3' non-translated sequence that functions in said plant cell to cause the termination of transcription and the addition of polyadenylated ribonucleotides to said 3' end of said mRNA molecule.

4. The transformed seed according to claim 3, wherein said seed is selected from the group consisting of soybean, maize, cotton and wheat seed.

5. The transformed seed according to claim 3, wherein said exogenous promoter region functions in a seed cell.

6. The transformed seed according to claim 3, wherein said exogenous promoter region functions in a leaf cell.

7. The transformed plant according to claim 1, wherein said nucleic acid sequence is SEQ ID NO: 1562.

8. The transformed seed according to claim 3, wherein said nucleic acid sequence is SEQ ID NO: 1562.

* * * * *